(12) United States Patent
Forsberg et al.

(10) Patent No.: US 6,168,758 B1
(45) Date of Patent: *Jan. 2, 2001

(54) LIQUID SAMPLE ASSAY DEVICE

(75) Inventors: Bengt Erik Forsberg, Etobicoke; Malcolm Francis Cox, Jr., Brampton; Charles Terence Macartney, Georgetown, all of (CA)

(73) Assignee: Starplex Scientific, Etibicoke (CA)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/974,617

(22) Filed: Nov. 19, 1997

(51) Int. Cl.[7] .................................................. G01N 33/48
(52) U.S. Cl. ............................ 422/61; 422/58; 422/102; 422/103
(58) Field of Search .................................. 422/56, 58, 61, 422/102, 103

(56) References Cited

U.S. PATENT DOCUMENTS

| | | | |
|---|---|---|---|
| 2,929,687 | * | 3/1960 | Buchoff .................................. 422/58 |
| 3,715,189 | * | 2/1973 | Nighohossian et al. ............... 422/61 |
| 3,741,727 | * | 6/1973 | Stroterhoff ............................. 422/58 |
| 3,992,158 | * | 11/1976 | Przybylowicz et al. .............. 422/58 |
| 4,473,530 | * | 9/1984 | Villa-Real ............................ 422/104 |
| 4,494,581 | * | 1/1985 | Gordon ................................. 422/102 |
| 5,013,667 | * | 5/1991 | Lynn et al. ............................. 422/61 |
| 5,238,652 | * | 8/1993 | Sun et al. . | |
| 5,403,511 | * | 4/1995 | Onishi et al. . | |
| 5,403,551 | * | 4/1995 | Galloway et al. . | |
| 5,429,804 | * | 7/1995 | Sayles . | |
| 5,658,531 | * | 8/1997 | Cope et al. ........................... 422/102 |

* cited by examiner

Primary Examiner—Lyle A. Alexander
(74) Attorney, Agent, or Firm—Merchant & Gould P.C.

(57) ABSTRACT

An assay device for determining the presence of specific analytes in a liquid sample comprises a container for collecting the sample liquid and a removable cap for sealing the container. The cap includes one or more test strips, such as chromatography strips, supported thereon for visually displaying the results of the assay. A reservoir attached to the underside of the cap, collects, through a passageway, a predetermined volume of liquid from the container when it is inverted thereby submerging the reservoir in the sample liquid. The liquid collected in the reservoir is transferred to the chromatography strips by a wicking system. A valve member located in the reservoir automatically swells upon absorbing a portion of the liquid in the reservoir. Such swelling causes the valve member to close the passageway to form a hermetic seal between the liquid contained within the container and the outside thereby preventing such liquid from becoming contaminated and any leakage of the contained liquid.

28 Claims, 13 Drawing Sheets

LIQUID SAMPLE ASSAY DEVICE

FIELD OF THE INVENTION

The present invention relates to liquid assay devices, and in particular, to liquid sample containers which include a self contained means of assaying such liquid.

DESCRIPTION OF THE PRIOR ART

There is presently a great demand for safe, reliable and easy to use liquid assaying devices. Such devices have uses in a variety of areas such as diagnostic testing of biological fluids, testing of water samples, etc. An example of one such application of the device is in diagnostic and drug testing purposes of urine samples at the screening stage. Screening apparatuses are used by health practitioners as a diagnostic aid. A preliminary assay will help the practitioner to determine the presence of various antigens in a patient's bodily liquids which could, potentially be causing an illness. There is even a greater demand for such diagnostic screening apparatuses due to a widespread fear which has been aroused in the general population by the growing number of people being infected with HIV. Due to the long incubation period of this disease many people have chosen to be screened so that early treatment can be obtained and the spread of this deadly disease can be reduced.

In society at large, there is also a growing concern about drug abuse. It is the policy of many employers to screen employees for the use of illegal drugs. Similarly, athletes are now routinely screened for the presence of banned substances both before and after competitions. To address the need to quickly screen people for these illegal substances, various screening devices have been produced which require manual transfer of a sample liquid from a collecting vessel to an assaying device. A positive test at the screening stage would require the sample to be sealed and then forwarded to a laboratory for more rigorous and complete testing to verify the results of the screening test.

One such device for specifically testing for the presence of non-protein antigens such as most drugs of abuse, is taught by U.S. Pat. No. 5,238,652. This device utilizes a thin layer chromatography membrane for testing for the presence of certain illegal drugs. The assaying device taught makes use of colored latex spheres combined with a specific antibody for binding to a specific antigen (i.e. drug). The latex spheres are applied to a chromatography membrane upstream of an immobilized drug conjugate probe. The antibody/latex complex is picked up by the test liquid and is used to indicate the presence or absence of a specific antigen drug. A positive test is indicated by the absence of a colored line in the area of the drug conjugate probe on the chromatography membrane due to the fact that the antibody will have bound the antigen rendering it unable to bind the drug conjugate probe. A negative test is indicated by a colored line corresponding to the binding of the latex/antibody complex to the drug conjugate probe.

In use, urine drops are withdrawn manually from a collection vial and added drop-wise to a reception cavity on the device. The urine is then absorbed by a pad and moves along the chromatography membrane by capillary action. This particular device is problematic in that the sample liquid must be manually transferred from the collection device to the assay device, being the chromatography membrane. This is dangerous to those conducting the assay as there is exposure to the sample which could include harmful materials. Also, the test sample is subject to contamination in the transferring process which reduces the reliability of the assay.

U.S. Pat. No. 5,403,551 teaches an assaying apparatus which also uses a chromatography membrane to indicate the presence or absence of specific antigens. As before the use of a latex/antibody complex will display a colored line in the absence of a specific analyte.

This assaying apparatus comprises a collecting vessel and an assaying device as one unit. A sample is introduced into a collecting chamber which is then sealed with a cap. The sample is then introduced into a reservoir through a flow path which is only accessible to the liquid sample when the device is inverted. The reservoir communicates with chromatography test strips and is sized to contain only enough samples to wet the chromatography membranes without flooding them. A mechanical valve is operated by twisting the cap of the device in order to close the flow path of the sample into the reservoir. In this way the sample liquid in the container is sealed off from the ambient air surrounding the container.

This apparatus has a drawback in that it is necessary for a person conducting the assay to remember to twist the cap and thereby close the mechanical valve after inverting the device. A failure to carry out this third step will result in the sample liquid in the container being contaminated by impurities in the ambient air surrounding the apparatus. This apparatus also has a further problem in that it is possible to inadvertently close the mechanical valve prior to inverting the apparatus to start the test. This results in the test not being properly started upon inverting the apparatus. The operator will then waste time waiting for the test to begin before realizing that the valve has been closed. The structure taught by U.S. Pat. No. 5,403,511 suffers from a further drawback in that it is complicated, involving several structural parts. This apparatus is therefore difficult and expensive to manufacture.

As such, there is a need for an assaying apparatus transferred to an assaying device included in the apparatus, without having to remove the sample liquid from the apparatus. A device is needed which has an automatic shut-off valve for preventing contamination of the sample liquid after the assay has been commenced. The automatic properties of such a valve would effectively eliminate the potential for human error in operating such a valve.

There is also a need for a simpler assaying device which is easier and less expensive to manufacture, which accomplishes the function of transferring liquid from a collecting medium to an assaying system without having to manually transfer the sample liquid, thereby exposing the sample liquid to the external environment.

SUMMARY OF THE INVENTION

The present invention is an apparatus, having an assaying device for conducting an assay on a sample liquid. The apparatus has means for collecting a sample liquid and means for transferring a predetermined volume of the collected sample liquid to the assaying device. The apparatus has an automatic valve for sealing the sample liquid in the apparatus from the external environment after the assay has been commenced.

According to one aspect of the invention, an apparatus is provided for conducting an assay on a sample liquid. The apparatus includes a container defining a chamber, the container having an open end for collecting a sample liquid. The apparatus has a removable cap for closing the container. An assaying device is included in the apparatus located on one of the cap and the container for visual observation thereof, the assaying device leaving means for receiving and chemically analyzing the sample liquid and visually displaying the presence of a specific analyte in the sample liquid. The apparatus further includes a defined sub-chamber communicating with the assaying device. The reservoir has a wall which defines at least one opening located to collect a predetermined volume of sample liquid inside the sub-chamber upon submerging the reservoir in the sample liquid in the container. The apparatus also includes a valve member which is located between the reservoir sub-chamber and the assaying device. The valve member is formed of a material that absorbs sample liquid and swells thereby closing off the assaying device from the sub-chamber after a predetermined amount of sample liquid is received by the assaying device.

According to another aspect of the invention, there is provided an apparatus for conducting an assay on a liquid located in a container. The apparatus comprises a cap for closing the container. The apparatus includes an assaying device located on the cap for visual observation thereof. The assaying device has means for receiving and chemically analyzing a sample liquid and visually displaying the presence of a specific analyte in the sample liquid. A reservoir is attached to the cap. The reservoir defines a chamber communicating with the assaying device, the reservoir having a wall defining at least one opening located to collect a predetermined volume of sample liquid inside the chamber upon submerging the reservoir in the sample liquid. The apparatus has a valve member located between the reservoir chamber and the assaying device, the valve member being formed of a material that absorbs sample liquid and swells thereby closing off the assaying device from the chamber after a predetermined amount of sample liquid is received by the assaying device.

According to another aspect of the invention there is provided a method of conducting an assay on a liquid comprising the step of providing a container for collecting a liquid sample to be assayed. The method includes the further step of segregating a predetermined amount of the liquid to be assayed from the remainder of the collected sample liquid by providing a barrier between the predetermined amount of liquid and the remainder of the collected sample liquid, the barrier being expandable upon contact with the liquid. The method includes the further step of contacting the predetermined amount of liquid with an assaying device including a chromatography strip having means for chemically analyzing a liquid for a specific analyte. The method includes the further step of expanding the barrier to hermetically seal off the remainder of the collected liquid.

In another embodiment, the invention provides an assay device for a liquid contained within a container, the device comprising a removable cap for the container, the cap having:
 a reservoir to receive a sample of the liquid from the container;
 a passage for transferring the sample of liquid from the container to the reservoir;
 a means for closing the passage;
 a means for assaying the liquid sample;
 a means for transferring the liquid sample from the reservoir to the means for assaying.

More particularly, the invention provides in one embodiment an assay device for a liquid contained within a container, the device comprising a removable cap for the container, the cap having:
 a reservoir to receive a sample of the liquid from the container;
 a passage for transferring the sample of liquid from the container to the reservoir;
 a valve for closing the passage;
 a plurality of chromatographic test strips for assaying the liquid sample;
 a wick for transferring the liquid sample from the reservoir to the test strips.

The invention also provides a method of using such device.

BRIEF DESCRIPTION OF THE DRAWINGS

These and other features of the preferred embodiments of the invention will become more apparent in the following detailed description in which reference is made to the appended drawings wherein.

DETAILED DESCRIPTION OF THE PREFERRED EMBODIMENTS

Figures 1, 2:
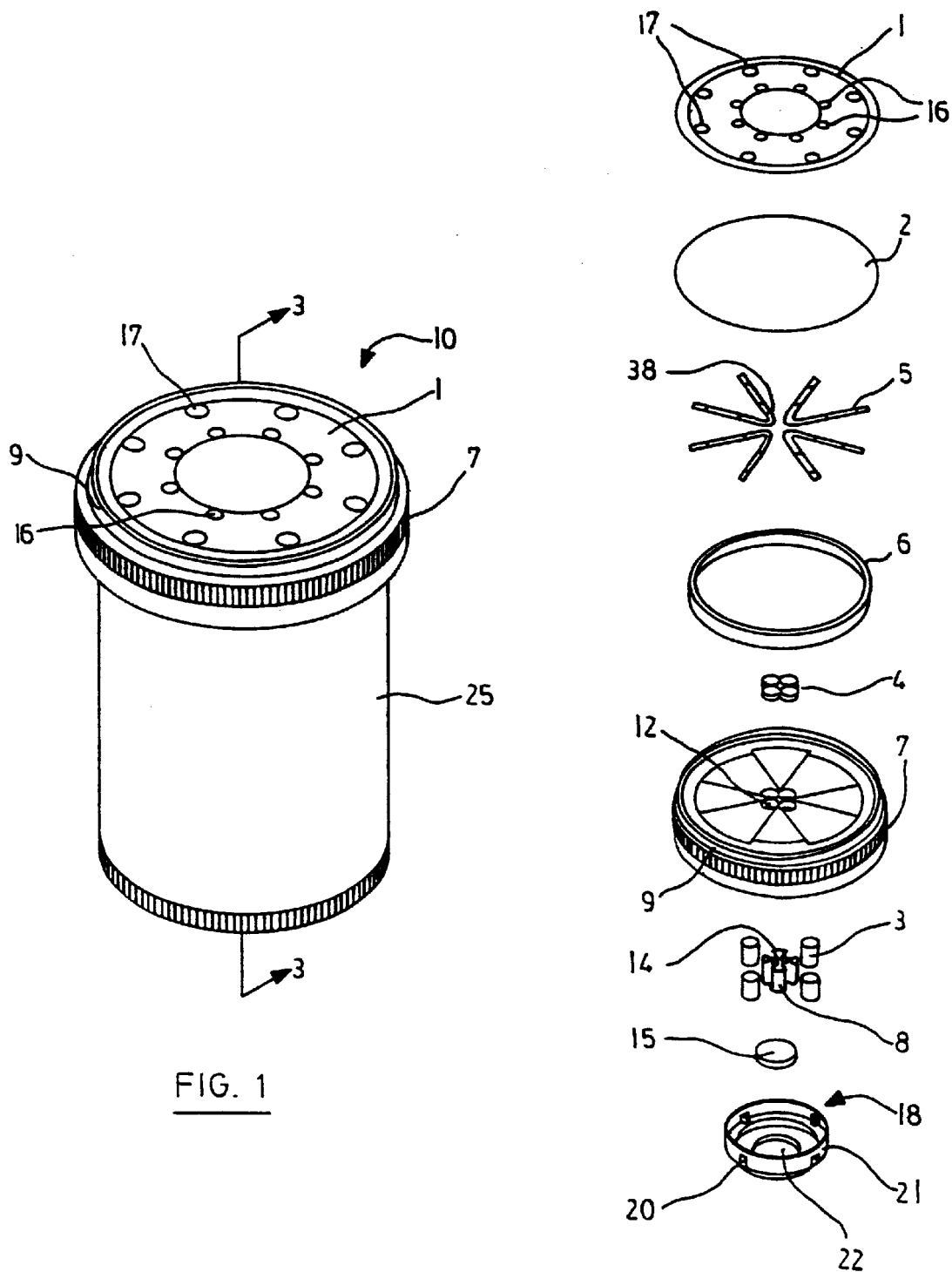
FIG. 1 is a perspective view of a preferred embodiment of an apparatus according to the present invention.
FIG. 2 is an exploded perspective view of the cap used in the apparatus of FIG. 1.
Figure 3:
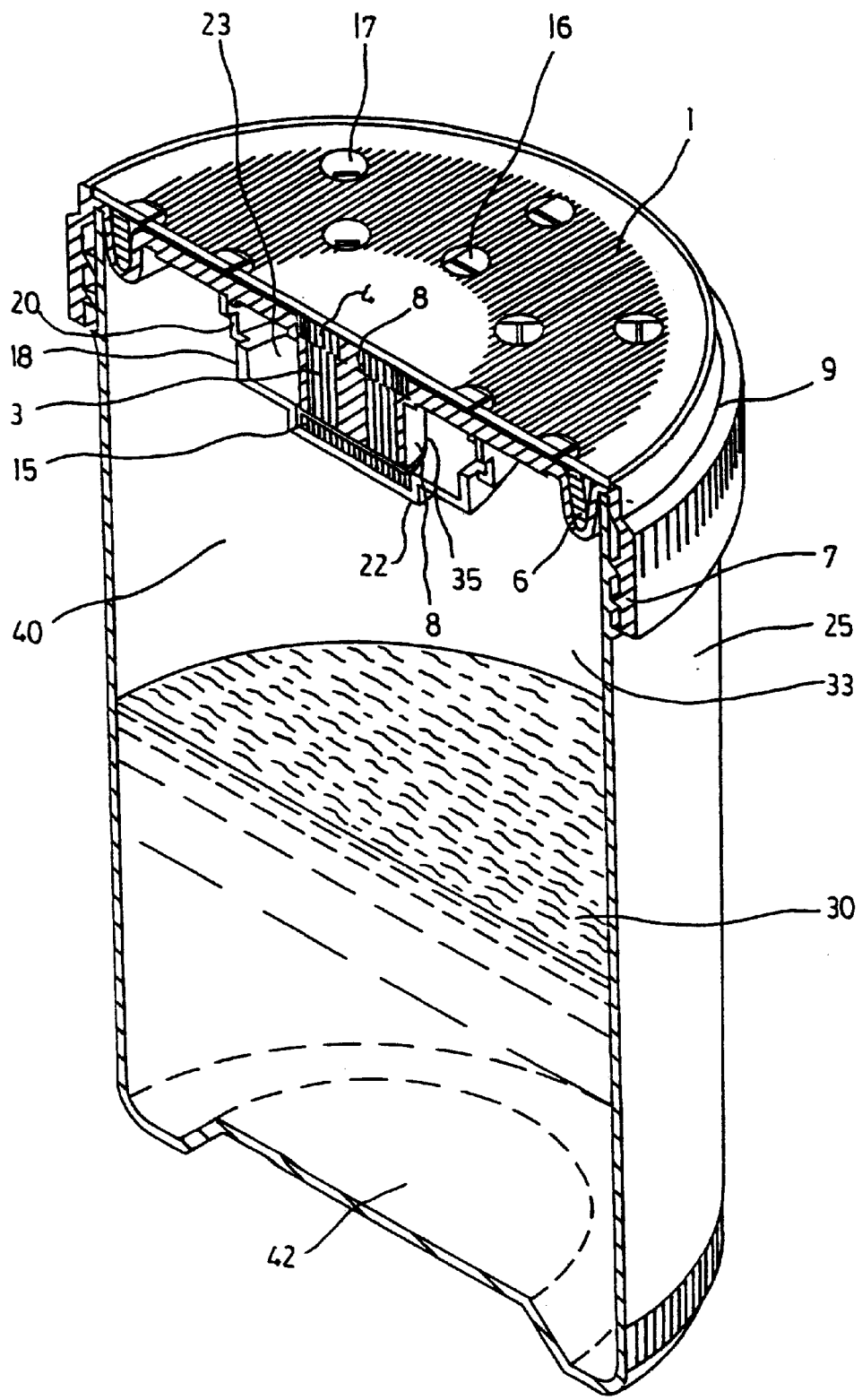
FIG. 3 is a cross-sectional view of the apparatus taken along lines 3—3 of FIG. 1 depicting the apparatus in a first operating position.

Referring to the drawings, an apparatus according to the present invention is generally indicated by numeral 10 as shown in FIGS. 1 to 3. Apparatus 10 includes a container 25 which defines a chamber 33. The chamber 33 functions to hold a quantity of a sample liquid 30 as depicted in FIGS. 3, 4 and 5.

Apparatus 10 includes a removable cap 7 which screws onto the container 25 in order to close the container. Preferably, the container has screw threads formed into it near an opening at the top of the container. The cap has a cylindrical portion 8 which extends downwardly from a bottom central portion of the cap. The cylindrical portion 8 is molded to the cap to form a single molded part including the cap and the cylindrical portion 8. In an alternate embodiment the cylindrical portion and the cap can comprise two separate parts which are tightly attached together.

Figure 4:
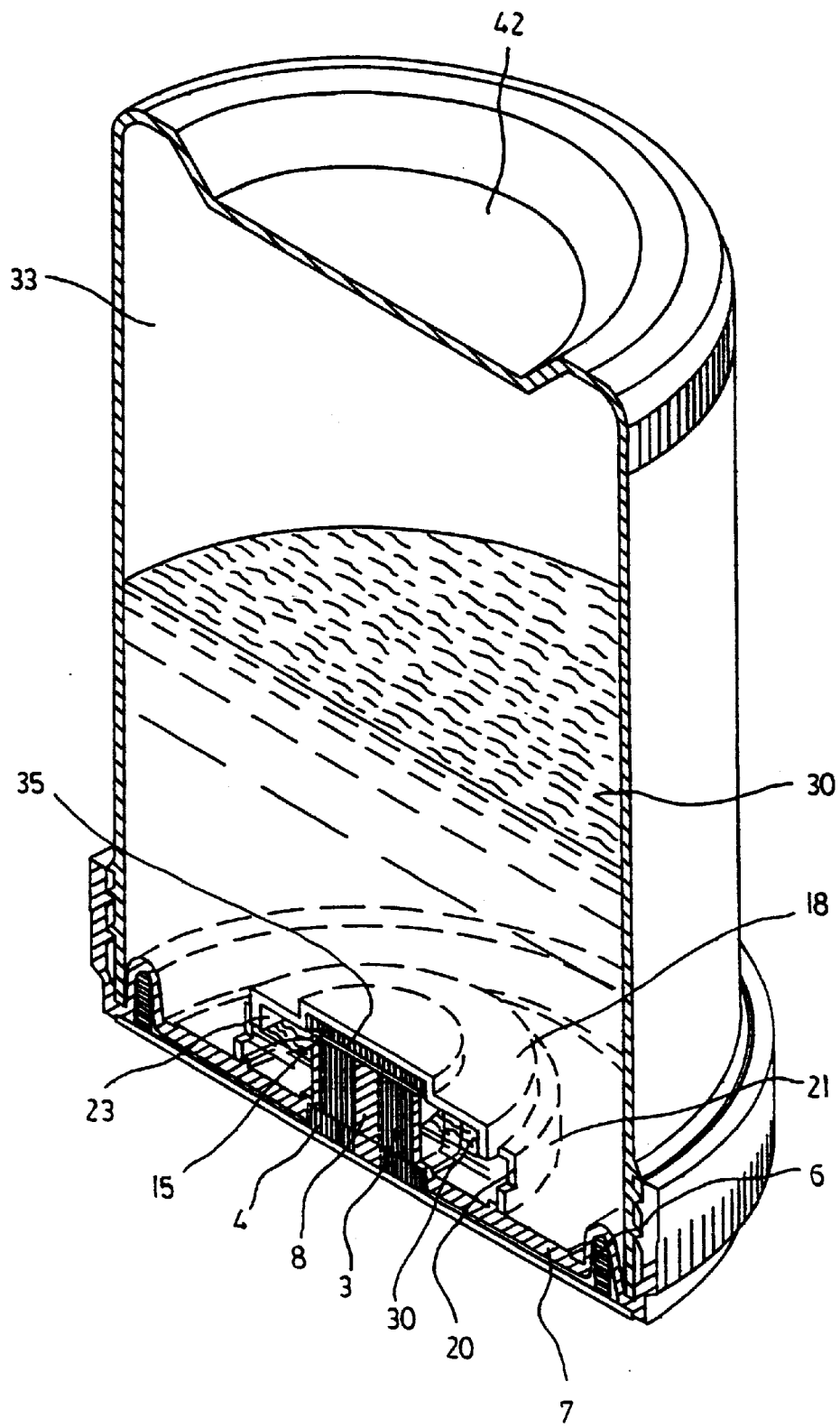
FIG. 4 is a cross-sectional view of the apparatus taken along lines 3—3 of FIG. 1 depicting the apparatus in a second operating position.
Figure 5:
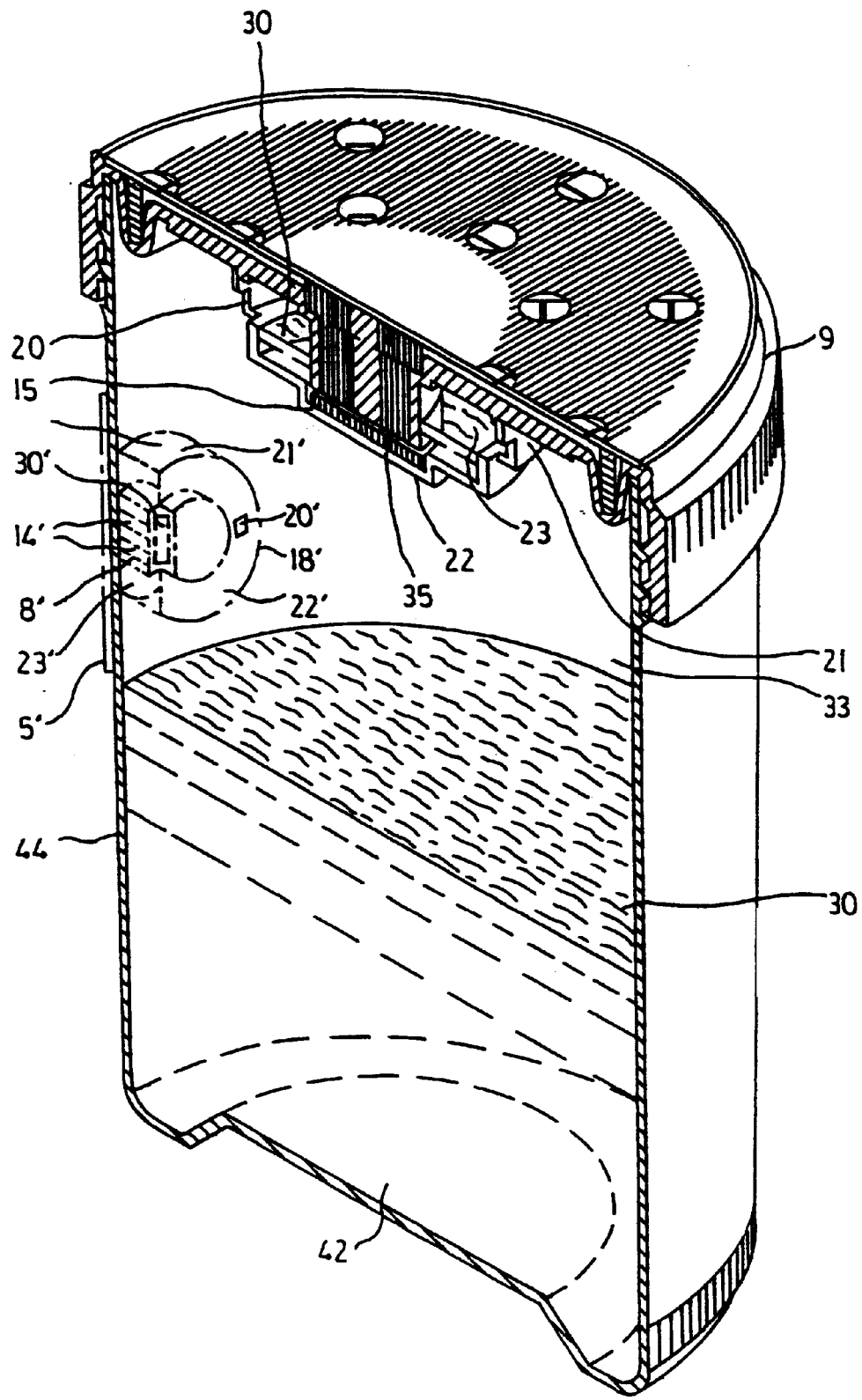
FIG. 5 is a cross-sectional view of the apparatus taken along lines 3—3 of FIG. 1 depicting the apparatus in a third operating position.

A reservoir 18 is attached to a bottom surface of the cap when the cap 7 is screwed onto the container 25, the reservoir 18 defines a sub-chamber 23 in the chamber 33 as shown in FIGS. 3, 4 and 5. The cylindrical portion 8 of the cap 7 is located in the sub-chamber. The reservoir has four openings 20 formed in a wall 21 of the reservoir 18. The openings 20 are of a sufficient size to allow a sample liquid 30 to flow into the reservoir 18 when the reservoir is submerged in the sample liquid 30. It is possible to have one or more openings 20 in the wall 21 of the reservoir. A greater number of openings will increase the rate at which liquid will flow into the sub-chamber 23 upon submerging the sub-chamber in the sample liquid in the container. Similarly the rate at which the sample liquid will flow out of the sub-chamber through the openings 20 will be proportional to the number of openings and the size of the openings formed in the wall 21.

The openings on the reservoir wall 21 are located at a common level with respect to a base 22 of the reservoir 18. It is not necessary that the openings 20 all be at the same level on the wall 21 with respect to the base 22, and other embodiments are possible where the openings are at varying levels on the wall 21 with respect to the base. However, the location of the opening 20 nearest to the base 22 will determine the ultimate level of the sample liquid 30 which will be collected in the sub-chamber 23 after inverting the apparatus, as discussed in more detail below. Hence, it is possible to predetermine the amount of sample liquid which will be collected in the sub-chamber 23, upon submersion of the reservoir in the sample liquid, by selecting the location of openings 20 on the wall 21. By placing the openings further upwardly from the base 22, more sample liquid will be collected in the sub-chamber 23. Conversely, less liquid will be collected in the sub-chamber when the openings 20 are located closer to the base 22. As will be discussed below, the volume of liquid collected in the sub-chamber will also be related to the air pressure which is within the reservoir 18 during filling of the sub-chamber.

The openings 20 are positioned on the wall 21 relative to the base 22 such that a volume of sample liquid will be collected in the sub-chamber 23 which will be sufficient to allow the assay to be conducted reliably. However, the volume of sample liquid collected will be sufficiently small so that an assaying device will not become flooded thereby adversely affecting the test results.

The reservoir 18 is attached to the cap 7. Many methods of attachment known in the art are possible for attaching the reservoir to the cap. The cylindrical portion 8 of the cap 7 has a plurality of passageways 14 formed therein (see FIG. 1). These passageways 14 extend from a bottom end of the cylindrical potion 8 of the cap through a top surface the cap 7.

At least one liquid permeable wick 3 is provided for transporting the sample liquid through the passageway 14. The wicks 3 transport the sample liquid 30, by capillary action, from the reservoir to a plurality of wick pads 4, as discussed in more detail below. The wicks 3 are formed of a cellulose based porous material, such as cellulose fibers which allows an aqueous liquid to be absorbed by the wicks and move through the wicks 3 by capillary action. Alternate embodiments are contemplated where the wicks are formed of other materials which will absorb and transport a liquid through capillary action.

The wicks are impregnated with colored latex spheres for the purpose of conducting an assay which is explained below. Since the material with which the wicks are impregnated is assay specific, alternate embodiments are contemplated in which the wicks are impregnated with materials other than latex spheres for the purposes of conducting different assays. Depending on the assay being performed in an alternate embodiment, it may not be necessary to impregnate the wicks with any material.

As discussed below, the composition of the wicks is dependent upon the type of tests being conducted on the sample. If only a single type of test is being conducted, it will be understood that only one wick would be required. Similarly, one wick can be used to supply liquid to a plurality of test strips. In such case, the cylindrical portion 8 would require only one passageway 14 located, preferably, in the center thereof.

An indentation 12 is formed over each of the passageways 14 on the top surface of the cap 7. The indentations 12 are each sized to accept a wick pad 4 which is formed of a non-woven glass fibre material through which the sample liquid will move by capillary faction. The wick pads 4 are located adjacent to the assaying device which may comprise a plurality of known liquid test strips 5, and function to draw liquid up through the wicks 3 and to transfer sample liquid 30 to the test strips 5 which are located on the cap 7, as discussed further below. Other materials which can absorb and transfer a liquid via capillary action can comprise the wick pads in alternate embodiments. A perimeter wick 6 is located in a groove 9 on the top surface of the cap. The perimeter wick is comprised of a liquid absorbent material such as cellulose paper and is located adjacent to the test strips 5. The perimeter wick 6 functions to absorb sample liquid 30 from the test strips 5 thereby drawing the sample liquid 30 along the test strips 5. Further, perimeter wick 6 also serves to prevent the strips 5 from being flooded by the liquid being assayed. A wicking system comprising the wicks 3, the wick pads 4 and the perimeter wick 6 provides transferring means for transferring sample liquid 30 from the reservoir 18 to the test strips 5.

A valve member 15 is located adjacent to the base 22 of the reservoir 18, inside the sub-chamber 23. The valve member 15 is located adjacent to the cylindrical portion 8, and therefore the valve member 15 is located adjacent to the wicks 3. When the valve member is in a valve open position, a gap 35 exists between the cylindrical portion 8 of the cap and the valve member 15, as indicated in FIGS. 3 and 5.

The valve member 15 is formed of a cross-linked polymer which is hydrophilic. In one embodiment, the cross-linked polymer comprising the valve member is chosen from the family of polymers known as polyether block amides available from ATOCHEM under the trade-mark PEBAX. Other cross-linked polymers which are hydrophilic and which swell upon absorbing water could also be used to comprise the valve member. It is not necessary that the material comprising the valve member be a cross-linked polymer. Any material which absorbs liquid and swells and thus prevents further flow of sample liquid through cylindrical portion 8, can comprise the valve member in alternate embodiments of the invention. Other materials are also possible for the valve member depending upon the liquid being tested and the substance being assayed. For example, PEBAX functions sufficiently well with aqueous liquids. However, this material has been shown to absorb the active ingredient in marijuana, THC, and, therefore, a device using such valve would give a false negative result. A valve made from balsa wood on the other hand can also be used for aqueous liquids and does not bind with THC.

Other embodiments of the invention are contemplated which include a valve member constructed of a lyophilic sol or gel which can absorb either aqueous solvents or non-aqueous organic solvents. In either case, absorption of the liquid will result in swelling and closing of the valve member. Hence, materials which swell upon absorbing an oil based or organic liquid and which are impermeable to these liquids when fully swollen, can comprise the valve member in alternate embodiments. In another embodiment, the valve member 15 is made of a laminate having an expanding layer of balsa wood and a sealing layer of a polymer such as cross linked polyolefin. The choice of balsa wood is preferred in the case of aqueous liquids and where materials discussed above may bind with the analytes being tested for.

Figure 6:
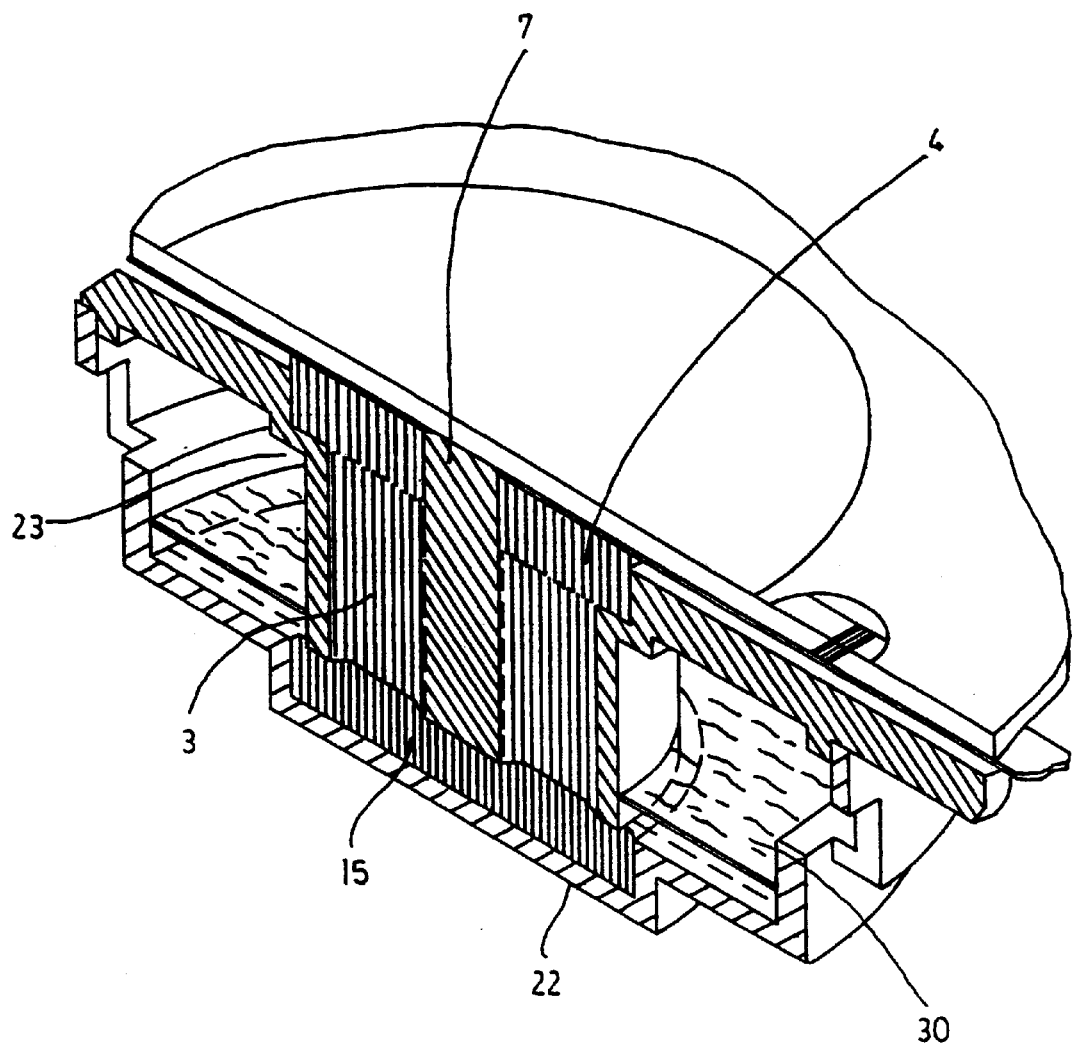
FIG. 6 is an enlarged cross-sectional view of a portion of the cap taken along lines 3—3 of FIG. 1 the apparatus in a fourth operating position.

The valve member 15 according to one embodiment of the present invention will absorb a water-based sample liquid 30 such as urine. Upon being submerged in the sample liquid the valve member will begin absorbing sample liquid 30. The valve member will swell gradually to a maximum expansion. This maximum expansion will be reached in approximately ten minutes. The valve member 15 is in a valve open position prior to the absorption of any liquid by the valve member 15. Before the valve member 15 has swelled to its maximum expansion, the gap 35 is present between the valve member 15 and the wicks 3. As such, sample liquid in the reservoir 18 will come into contact with the wicks 3 when the valve member is in the valve open position. When the valve member 15 has absorbed a sufficient amount of sample liquid to swell to its maximum expansion the valve member 15 will reach a valve closed position thereby closing the gap 35 as depicted in FIG. 6.

The valve member 15 serves various functions in the device. For example, when the valve member is in the valve closed position, it hermetically seals the sample liquid 30 in the chamber 33 and in the sub-chamber 23, from the ambient air outside of the apparatus 10. This prevents any contamination of the sample liquid located in the chamber 33, which may be required for testing at a later time. Such further testing may be required in the event that the results of the present testing device are to be verified. Such a hermetic seal, also prevents any more sample liquid from the reservoir from coming into contact with the wicks 3. As such, the movement of any sample liquid, remaining in the sub-chamber 23, to the test strips 5 is halted. Such sealing is also required in an embodiment of the invention where an air outlet is provided on the top surface of the cap. Such outlet is provided to relieve any pressure which may accumulate as the liquid is transported across the test strip. As will be appreciated, in an embodiment as shown in the figures, such pressure accumulation will occur along the outer perimeter of the cap. Therefore, the outlet would preferably comprise a gap along such outer perimeter. It will also be appreciated that such pressure may be quite minimal and, therefore, an outlet as described is required only as a contingency basis.

In another embodiment of the invention, the air outlet may comprise one or more holes (not shown) in the reservoir 18. Such holes will be designed such as to permit the passage of air therethrough while being small enough to prevent the passage of liquid. It will be appreciated that the sizing of such holes will be dependent upon the surface tension of the liquid being tested. It will also be appreciated that if such holes are provided in the reservoir 18, no additional air outlets would be required in the cap thereby resulting in the device being completely sealed without any leakage of the contents.

The valve member also functions to prevent any sample liquid in the container from being suctioned out of the container when the apparatus is stored in a low pressure compartment. This would otherwise be problematic in situations such as where the apparatus is stored in the cargo bay of an aircraft upon shipment of the apparatus to a laboratory for further testing. To relieve the pressure differential between the outside of the container and the inside of the container, it is contemplated to place a small pressure equalizing opening in the cap above the test strips, in an alternate embodiment. In such a case, an overcap could be placed above the cap.

In another alternate embodiment, it is contemplated to laminate a top surface of the valve member with a rubber or a lacquer coating in order to prevent the valve member from drying out in arid conditions.

A plurality of test strips 5 are located on the cap 7 and are thus readily visible. The test strips 5 provide an assaying device located on the cap of the container for visual observation thereof. In an alternate embodiment, as described below, the test strips 5 can be located on the container 25. The test strips 5 may comprise chromatographic, chemi-fluorescent or other known liquid assay strips. The test strips 5 have means for receiving the sample liquid 30. The means for receiving the sample liquid are ends of the test strips 5 which are in direct contact with the wick pads 4. In one embodiment, the test strips conduct chromatographic assays and four separate chromatography membranes 38 are provided on the cap. Each of the four chromatography membranes 38 comprise two chromatography strips 5. Hence there are eight chromatography strips 5 allowing for eight separate assays to be conducted on a sample liquid. Hence, it is possible to test for the presence of several different substances at the same time, while eight chromatography strips are shown in FIG. 1, a greater or lesser number of individual strips may be used depending on the desired number of tests to be run on the sample liquid 30. The chromatography membranes 38 are composed of a porous material through which the sample liquid will move by capillary action. Preferably the chromatography membranes are composed of a cellulose nitrate material.

Each of the chromatography strips 5 is impregnated with a test antigen conjugate probe which is immobilized at a fixed location on the chromatography strip 5. The test chemical structure to the specific antigen, such as cocaine or heroin, which is being tested for by that particular chromatography strip 5. A test antigen conjugate probe is a molecule having the same or similar chemical structure as the substance which is being tested for. The active site on a conjugate probe will generally be anchored to a larger molecule but will be available to bind all antibody which has been sensitized to the antigen for which the test is being directed.

A second probe, or control or test valid probe, is immobilized at a location downstream on the chromatography strip 5 of the test antigen conjugate probe. The second probe is a protein antigen conjugate probe. The antibodies are sensitized to have a second site which will bind the protein antigen conjugate probe. As mentioned previously, the wicks 3 are soaked in latex which consists of colored microscopic latex spheres which are coated with the antibodies sensitized to bind the specific antigen and the protein antigen conjugate probe. The latex spheres may be about 0.1 to about 1 micron in diameter and may be one of many colors. The spheres are only visible when concentrated together in large numbers. The latex spheres are impregnated on the wicks 3 such that they are immobilized prior to coming into contact with the sample liquid 30. As the sample liquid moves along the wicks 3, the sample liquid 30 will eventually come into contact with the latex spheres. The latex spheres become mobilized upon coming into contact with the sample liquid 30 and are carried with the sample liquid as the sample liquid moves along the wicks, through the wick pads, and eventually along the chromatography strips 5.

If the sample liquid contains none of the specific antigen being tested for, then the antibodies attached to the latex spheres will bind the test antigen conjugate probe thereby forming a complex consisting of the test antigen conjugate probe and the latex spheres at the site of impregnation of the test antigen conjugate probe on the chromatography strip 5. This will give rise to the appearance of a colored line at the site of impregnation of the test antigen conjugate probe.

The remaining latex spheres which pass the test antigen conjugate probe after the binding sites on the test antigen conjugate probe have become saturated, will bind to the protein antigen conjugate probe located further downstream along the chromatography strip 5. This will give rise to a second colored line at the site of impregnation of the protein antigen conjugate probe. The purpose of the second colored line is to indicate that the test is active. Hence a negative test will give rise to two colored lines on the chromatography strip.

In the event that the test antigen is present in the sample liquid 30, then the antibodies on the latex spheres will bind to the test antigen molecules immediately upon the sample liquid coming into contact with the latex spheres on the wick 3. The active site on the antibody for binding the test antigen will then not be available for binding the test antigen conjugate probe on the chromatography strip 5. As such, the latex spheres will pass over the site of impregnation of the test antigen conjugate probe. As a result, no line will be formed at that site. The antibodies will however, bind to the protein antigen conjugate probe further downstream to indicate that the test is active. Hence, a positive test will be indicated by the presence of a single colored line located at the site of impregnation of the protein antigen conjugate probe on the chromatography strip 5.

It should be appreciated that an immunoassay can be conducted with substances other than latex spheres. One alternative is to use colloidal gold particles in the place of latex spheres. It will be appreciated to those knowledgeable in the art that many different types of assays may be conducted with the apparatus 10 which may or may not be immunoassays as described above. Such assays will depend on the test strips used.

In the above example, a plurality of test strips are provided on the device. In another embodiment, designed for a specific application, only one test strip may be required. An example of such embodiment is an assay device designed for testing the presence of a particular substance in water or urine samples.

A transparent protective cover 2 is placed over the chromatography strips 5 on the cap 7 in order to provide a protective barrier for the chromatography strips to prevent them from becoming contaminated by substances which may be suspended in the ambient air surrounding the chromatography strips. A label 1 is placed over the protective cover 2 for indicating which specific antigen is being tested for on each individual chromatography strip 5. The label also functions to emphasize the results of the assay. The label has a plurality of openings 16 corresponding to the area on each chromatography strip 5 where the test antigen conjugate probe has been impregnated. Hence the appearance of a colored line at this site will be emphasized by an opening 16 on the label 1. A second group of openings 17 is formed in the label along the periphery of the label. Openings 17 overlap with the sections of the chromatography strips 5 which have been impregnated with the protein antigen conjugate probe. The openings 17 will emphasize the appearance of a colored band at this location on the chromatography strips 5 thereby indicating that the test is active.

In an alternate embodiment, the cover 2 and the label I can comprise a single integrally formed part. To achieve this result, the label could be silk screened or otherwise embossed onto the cover. Other methods known in the art are also possible for imprinting the label onto the cover.

To operate the apparatus 10, it is necessary firstly to remove the cap 7 from the container 25. The individual being tested will then fill the chamber 33 with a sample liquid which would normally be urine. Preferably, chamber 33 will be filled to approximately half of its volume with sample liquid 30. Once the chamber 33 has been filled with sample liquid, the cap 7 is screwed on tightly to the container 25 so that a hermetic seal is formed between the container 25 and the cap 7. The apparatus, in a first operating position, after the initial filling of the chamber 33 with sample liquid with the cap 7 securely attached to the container 25, is depicted in FIG. 3. It is apparent that the reservoir 18 defines a sub-chamber 23 in the chamber 33. At this stage of operation, the valve member 15 is in the valve open position. A gap 35 exists between the valve 15 and the wicks 3 which arc supported in the cylindrical portion 8 of the cap.

After the chamber 33 has been filled with sample liquid 30, it is then necessary to screw the cap onto the container and then to invert the apparatus in order to submerge the reservoir 18 in the sample liquid, in the chamber 33. FIG. 4 depicts the apparatus in an inverted position. The reservoir 18 is submerged in the sample liquid 30 upon the inversion of the apparatus 10. The sample liquid 30 enters into the reservoir through the openings 20 in the wall 21 of the reservoir 18. As the level of the sample liquid 30 in the reservoir sub-chamber 23 rises above the level of the openings 20, air in the sub-chamber 23 can no longer escape out of the sub-chamber through the openings 20. As such, a pressure-head is created between the rising sample liquid in the sub-chamber 23 and the air between the sample liquid 30 and the base 22 of the reservoir 18. The pressure-head created prevents the level of liquid in the inverted sub-chamber 23 from rising to a level sufficient to allow the wicks 3 to come into contact with the sample liquid 30. As such, the assay will not begin while the apparatus is in the inverted position. At this stage, the valve member is also not brought into contact with the sample liquid 30, hence the valve member 15 will not yet begin to swell thus remaining in the valve open position. As such there is still a gap 35 between the wicks 3 and the valve member 15.

As will be appreciated by those skilled in the art, the pressure head discussed above also forces the air within the reservoir through the wick 3 while the valve is still in the open position. The rate of such air passing through the wick will be dependent on the characteristics of the wick material such as its porosity and on the number of wicks present.

It will be understood that if the apparatus is maintained in the inverted position too long, enough air will be passed through the wick to allow the liquid level within the sub-chamber 23 to reach the bottom of the wick. In such case, the assay may commence prior to righting the container which may not be desired. Further, if the liquid is permitted to enter the wicks while the container is inverted and if such container includes an externally venting air outlet as described above, leakage of the liquid may result. For an apparatus as described herein, the time inverted is approximately fifteen to thirty seconds.

After maintaining the apparatus in the inverted position for the time mentioned above, a predetermined amount of liquid is collected in the sub-chamber 23, the apparatus is then reverted to the upright position as shown in FIG. 5. As mentioned above, the maximum time for maintaining the apparatus in such inverted position is dependent upon the porosity of the wick. The level of liquid retained in the sub-chamber will depend on the level of the openings 20 on the wall 21 of the reservoir 18, as excess sample liquid in the reservoir 18 will flow out of the sub-chamber 23 through openings 20. Hence the level of liquid remaining in the sub-chamber 23 after reversion of the apparatus will be determined by the location of the opening 20 on the wall 21 nearest to the base 22 of the reservoir. The predetermined volume of sample liquid collected inside the sub-chamber 23 is the volume of sample liquid remaining in the sub-chamber after the sample liquid has filtered out of openings 20 upon reversion of the apparatus to the upright position.

After returning the apparatus to its upright position, the valve member 15 becomes submerged in the sample liquid 30. Also, the gap 35 becomes filled with sample liquid bringing the wicks 3 into contact with the sample liquid thereby commencing the transfer of sample liquid to the chromatography strips. Once the valve member 15 becomes submerged in the sample liquid it begins to gradually absorb sample liquid and to swell. The valve member 15 will eventually seal off the gap 35. However, the valve will swell slowly enough so that the gap 35 will not be sealed by the valve 15 until the predetermined volume of liquid collected in the reservoir has been absorbed by wicks 3. The predetermined amount of sample liquid received by the assaying device before the valve member seals off the sub-chamber 23 from the assaying device will be determined by selecting the amount of sample liquid which can be collected by the sub-chamber 23 upon submerging it in the sample liquid in the chamber 33, as described above.

FIG. 6 depicts the valve member 15 in its fully expanded position where the valve member has closed gap 35 forming a hermetic seal between the reservoir sub-chamber 23 and the wicks 3. As such, a hermetic seal is formed between the sample liquid in chamber 33 and the ambient air outside the apparatus 10 so that the sample liquid 30 which may be subject to further testing cannot be contaminated after the assay has been completed.

The reservoir 18, upon inverting the apparatus 10 and then reverting the apparatus to its upright position, serves to segregate a predetermined amount of liquid to be assayed from the remainder of the collected sample liquid by providing a barrier between the predetermined amount of liquid and the remainder of the collected sample liquid. The barrier includes the valve member and it may be attached to the base of the reservoir. The barrier is therefore expandable upon contact with the liquid. The wicks 3 and the wick pads 4 provide means for contacting the predetermined amount of liquid with an assaying device including a chromatography strip having means for chemically analyzing a liquid for a specific analyte. The liquid absorbing and swelling properties of the valve member provides means for expanding the barrier to hermetically seal off the remainder of the collected sample liquid.

According to another embodiment of the present invention, the chromatography strips 5 which constitute the assaying device can be located on a sidewall 44 of the container 25 as indicated by strips shown in chain-dotted lines in FIG. 5. In this embodiment, the sidewall 44 has cylindrical portion 8' extending into the chamber 33. Attached to an interior surface of the sidewall 44 of the container 25 over the cylindrical portion is the reservoir 18'. As with the preferred embodiment, the cylindrical portion 8' defines a plurality of passageways 14', each passageway 14' supporting a wick which will extend from the reservoir sub-chamber 23' to the chromatography strips 5'. This embodiment is operated by first tilting or inverting the apparatus 10 and then placing the apparatus on its base 42 or a side of the sidewall opposite to the section of the sidewall to which the reservoir 18' is attached, so that excess sample liquid can flow out of the reservoir sub-chamber after it has been submerged in the sample liquid. If the apparatus is to be placed on its side after submerging the reservoir, the openings 20 in the reservoir would be in the sidewall 21' of the reservoir. However, if the apparatus is to be placed on the base of the container after submersion of the reservoir then the openings in the reservoir will be in the base 22' of the reservoir as indicated in FIG. 5. A valve member 30' is located in the reservoir sub-chamber between the cylindrical member 8' and the base 22' of the reservoir.

In yet another embodiment of the present invention, the chromatography strips 5 can be located on the base 42 of the apparatus 10. This embodiment would be like FIG. 4, but the cap would be enlarged and become the container, and the container would perform the function of the cap. To operate this embodiment, one would fill the container with sample liquid and then seal the container by putting on the cap. Inverting the apparatus would then allow the assay to proceed to completion as described above. The apparatus is not reverted to the upright position.

It will be appreciated by those skilled in the art that the apparatus 10 can be used for many applications other than screening bodily liquids for specific antigens. Among other applications, the apparatus can be used to test water samples from lakes and rivers for various pollutants. Also, an alternate embodiment of this invention can be used to test organic liquids such as oil samples for the presence of toxins such as PCBs.

Figure 7:
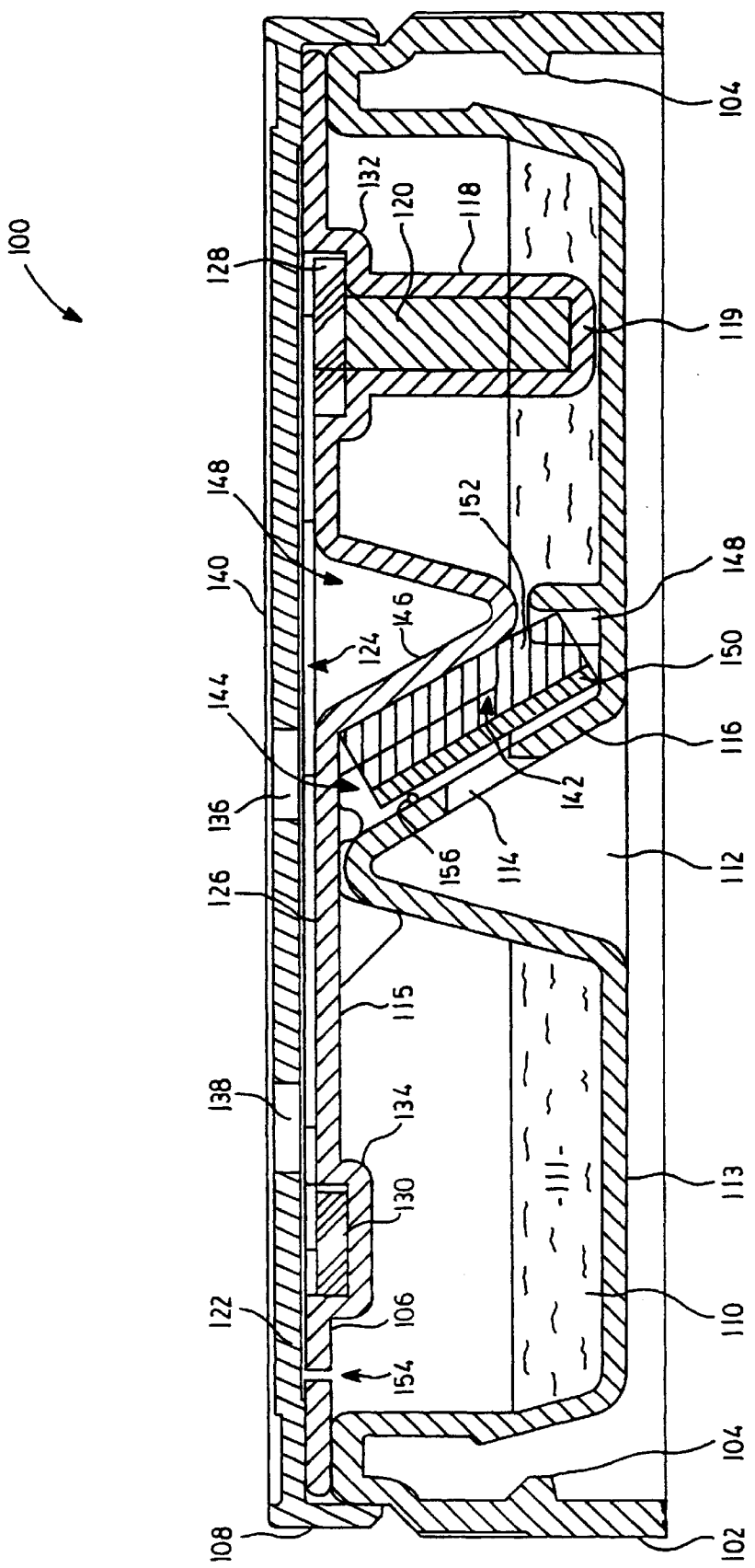
FIG. 7 is a side cross sectional view of a further embodiment of the invention.
Figure 8:
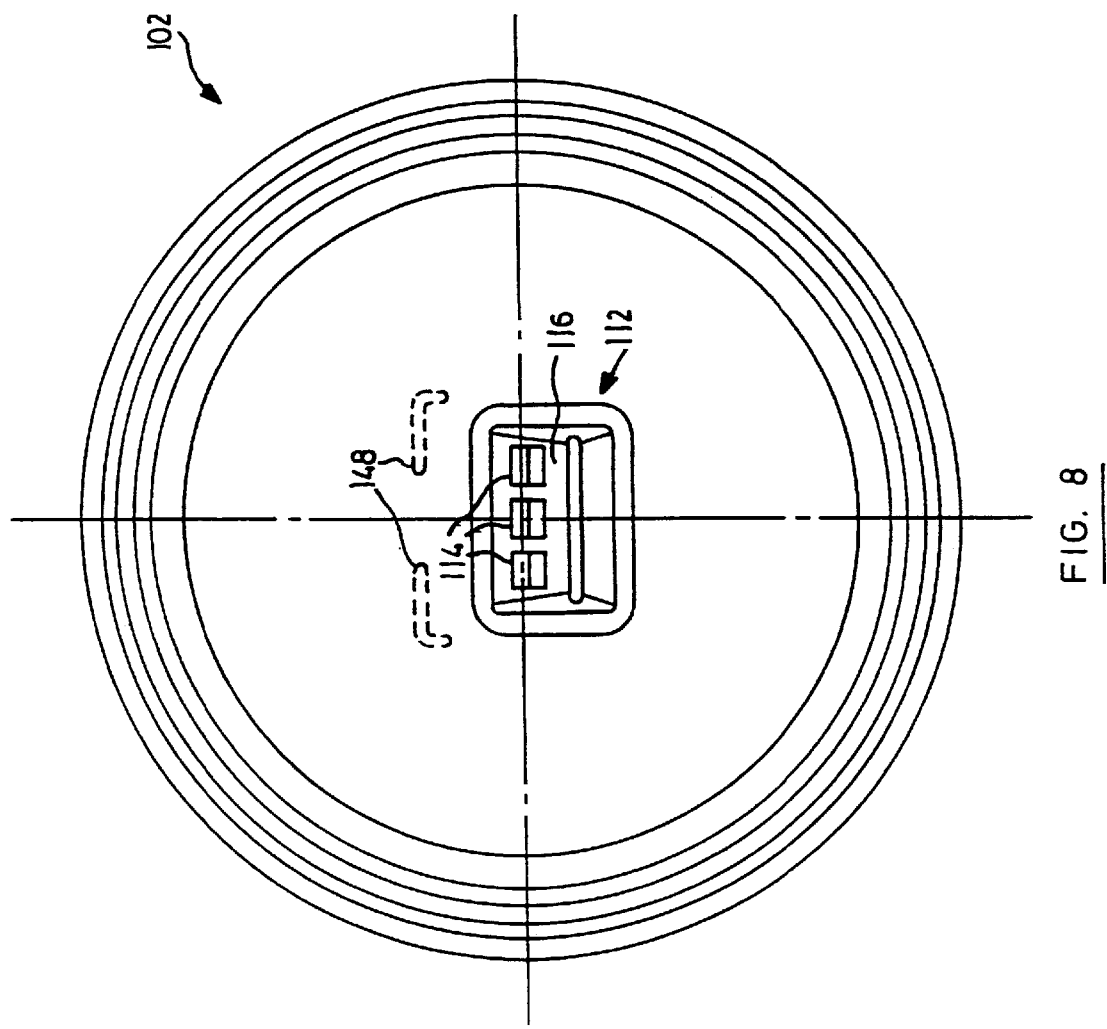
FIG. 8 is a bottom view of the embodiment of FIG. 7.

A further embodiment of the present invention is illustrated in FIG. 7. As with the embodiments discussed previously, the assaying device includes a container (not shown) as described above. A cap for the container is shown generally at 100. The cap 100 includes a base 102 preferably having a thread 104 for engaging a corresponding thread on the container as described above. The cap 100 further includes a middle portion 106 and a cover 108. The base 102 includes a bottom wall 113 which defines the bottom wall for a reservoir or well 110 for receiving a sample of the liquid contained within the container. Such sample of liquid is shown at 111 The base 102 also includes a liquid inlet portion 112. As shown in FIGS. 7 and 8, the inlet portion 112 is preferably rectangular in plan view and triangular in cross section. The inlet portion 112 includes a plurality of windows 114 on a side wall 116 thereof. The windows 114 allow liquid from within the container into the well 110. As will be explained below, in the preferred embodiment, the windows 114 are located approximately mid way along the height of the side wall 116 in order to permit a sufficient volume of the liquid to be collected within the well 110.

Figure 9:
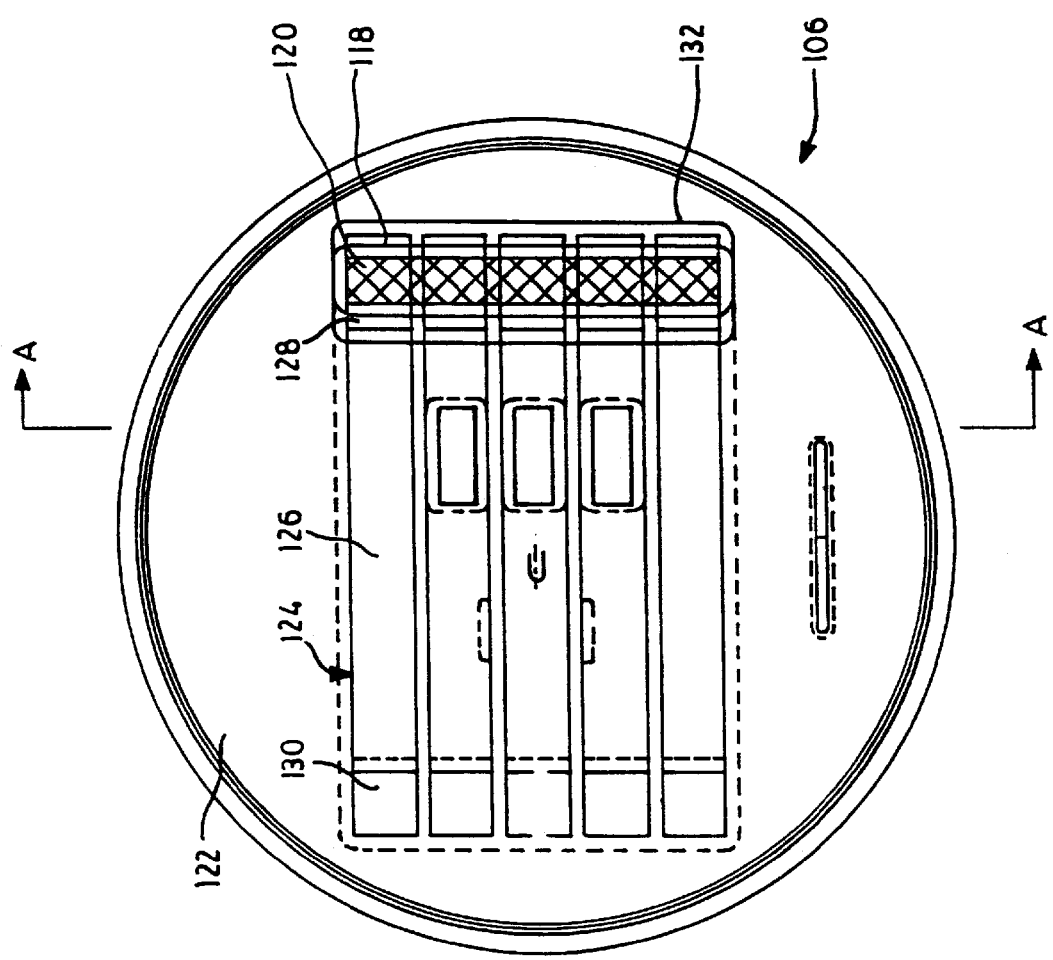
FIG. 9 is a plan view of the middle portion of the embodiment of FIG. 7.
Figure 13:
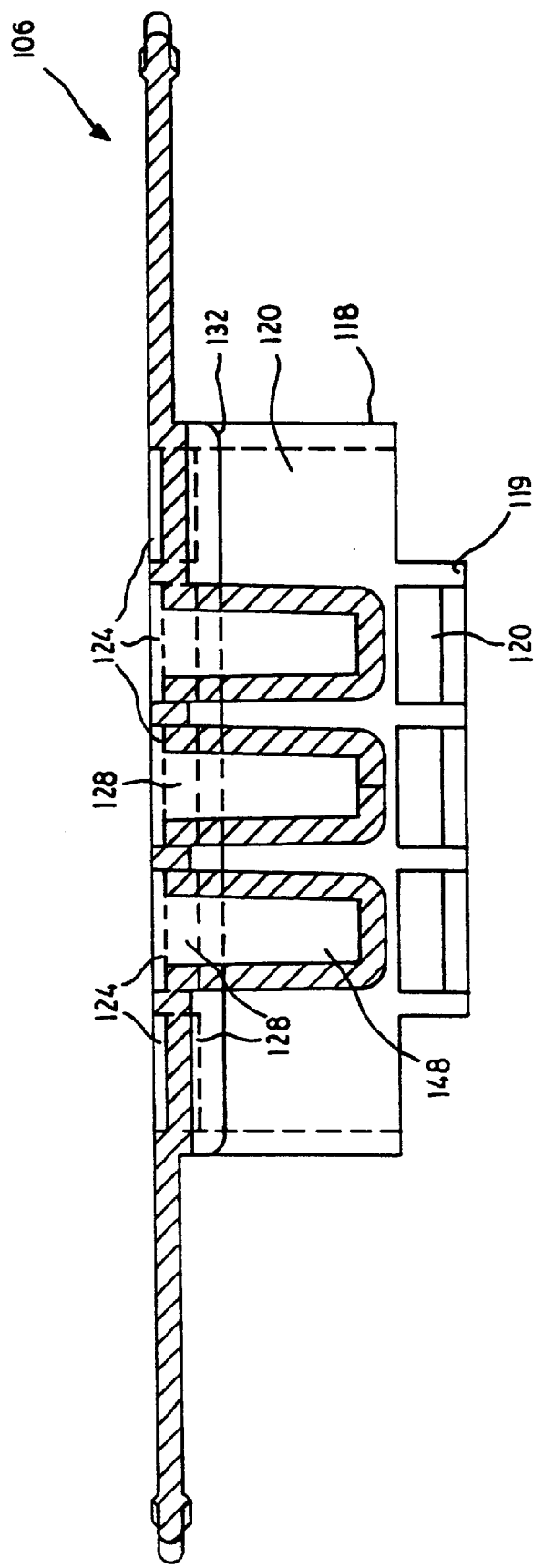
FIG. 13 is a side cross sectional view through A—A of FIG. 9.
Figure 15:
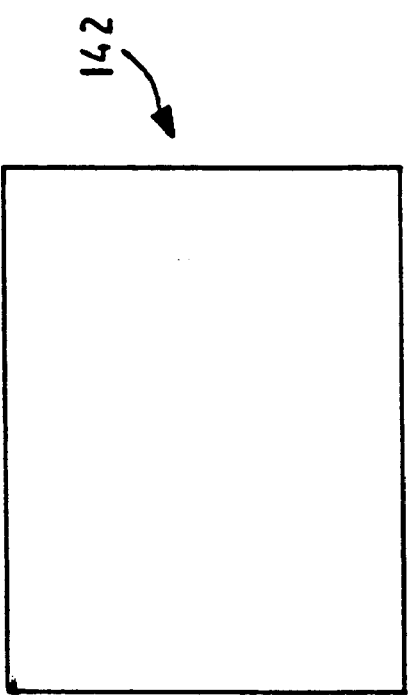
FIG. 15 is a front view of the pad of FIG. 14.

As shown in FIGS. 7 and 9, the middle portion 106 of the cap includes a bottom wall 115 which defines a top wall for the well 110. The middle portion 106 also includes an elongate wick chamber 118 containing a wick 120. The wick chamber 118 is located proximal to the outer diameter of the cap 100. The bottom portion of the chamber includes an opening from which depends a plurality of bars 119 preferably of a "U" shape which supports the wick 120. This arrangement is shown in FIG. 13. The opening in the bottom of the chamber 118 allowing the wick 120 to contact the sample of liquid 111 within the well 110 while the bars 119 maintain the wick in at fixed position. The wick 120 is made of a material which absorbs the liquid sample and transfers same by capillary action. Wick 120 is preferably in the form of a rectangular slab which extends across the length of the chamber 118. The appropriate material for the wick is dependent upon the liquid sample and the type of tests being conducted. The possible materials which can form the wick were discussed above.

Figure 10:
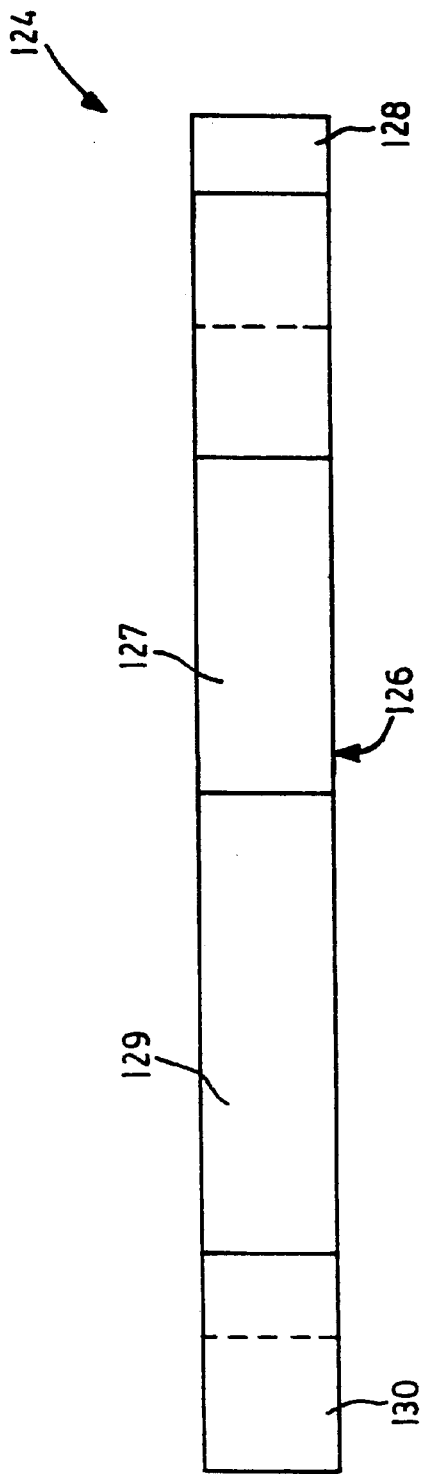
FIG. 10 is a plan view of a test strip for the embodiment of FIG. 7.
Figure 11:
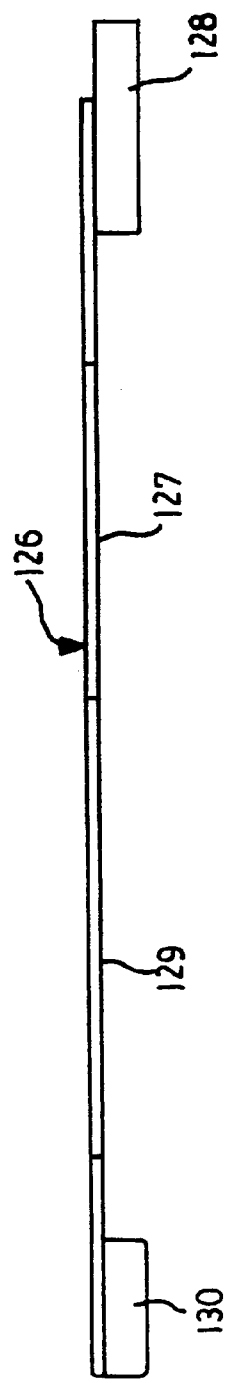
FIG. 11 is a side elevation of the test strip of FIG. 10.

The middle portion 106 supports, on the top surface 122, a plurality of test strips 124 for conducting the desired assays. As best shown in FIGS. 10 and 11, the test strips 124 include assay surface 126 and first and second wick pads 128 and 130, respectively. The assays surface 126 of the test strip are treated with various reagents depending upon the assay being conducted. Various conventional forms of test strips are possible for use in the present invention. Examples of such strips are provided above. In the usual case, the test comprises a chromatographic assay for the presence of a particular analyte in the liquid. In a preferred embodiment, the strips include an assay region 127 and a control region 129. The assay region 127 is provided with the reagents discussed above for conducting the desired assay. The control region 129 is provided with different reagents for ensuring that the test was conducted properly in that a sufficient volume of liquid was absorbed and contacted with the reagents. The test strips are made of an appropriately absorbent material which draws liquid across its surface thereby bringing such liquid into contact with the various reagents. By providing the assay device with a plurality of different test strips, various assays can be conducted simultaneously on a given sample. In one embodiment as shown in FIG. 11, the wick pads 128 and 130 are provided below the assay surface 126. In another embodiment, such wicks can be provided above the assay surface. In such case, the first wick 128 functions as a bridge linking the wick 120 to the assay surface 126 of the test strip 124.

Wick pads 128 and 130 are contained within first and second recesses 132 and 134 on the upper surface of the middle portion 106. First recess 132 is located above and opens into the wick chamber 118. In this manner, first wick pad 128 contacts the wick 120 and is wetted by same thereby drawing such liquid. In such manner, liquid 111 from the well 110 is supplied to the first wick pad 128 which then transfers the liquid to the test strip which, in turn, transfers the liquid to the second wick pad 130 where it is collected. In the preferred embodiment, second wick pad 130 for each test strip is provided proximal to the outer diameter of the cap 100 and opposite from the first wick pad 128. In this way, the length of the test strips is maximized over the surface of the cap 100. Second wick pad 130 draws liquid along the length of the test strip 124 and prevents flooding of same.

It will be understood that test strips as described above are generally known in the art. Accordingly, a variety of test strips can be utilized in the present invention. Such strips can, for example, be of a chromatographic or a chemiluminescent assay nature, and can be used to test for a variety substances in either aqueous or non-aqueous liquids.

Figure 12:
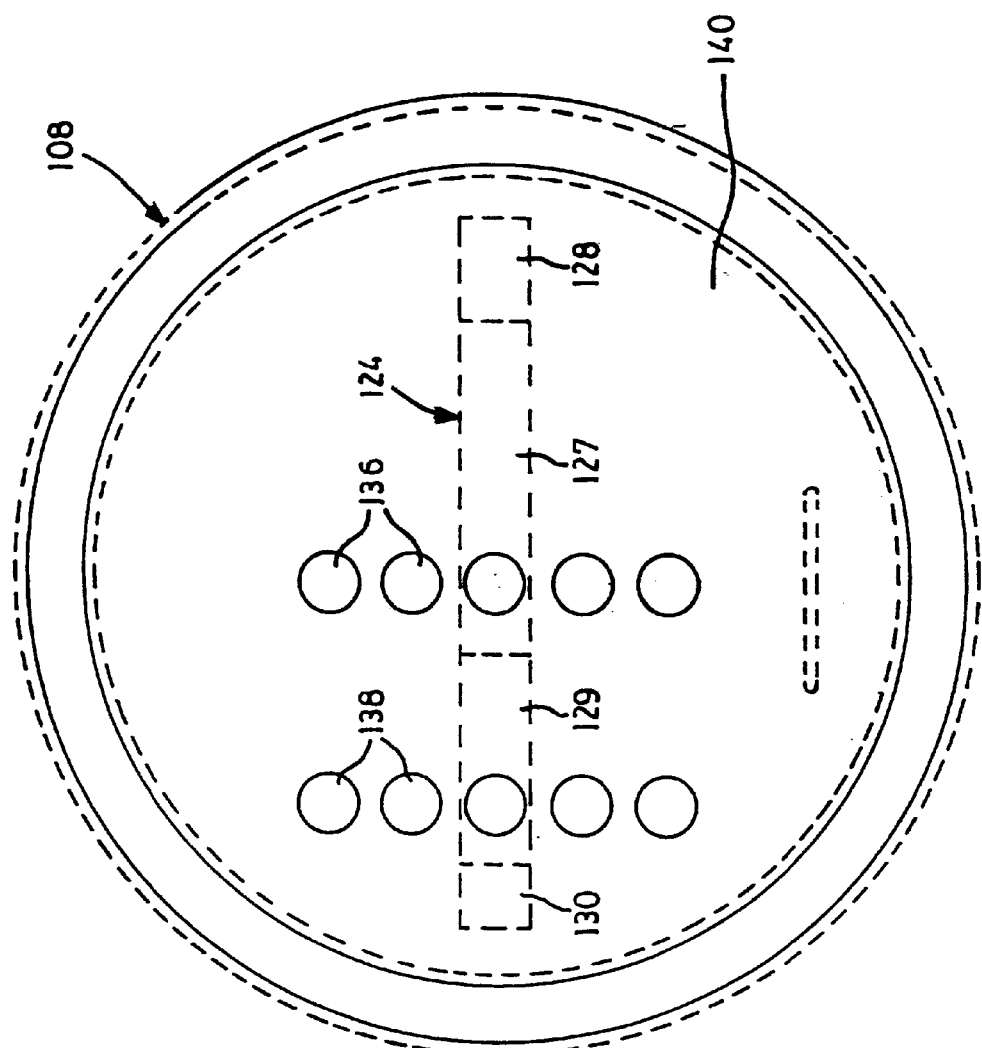
FIG. 12 is a plan view of the embodiment of FIG. 7 illustrating the cover portion.

As shown in FIGS. 7 and 12, the cover 108 is provided over the test strips 124 and protects such strips from contamination. The cover includes a plurality of first and second windows 136 and 138, respectively. First windows 136 are provided over the assay region 127 of the test strips 124 while second windows 138 are provided over the control region 129 of the test strips. In one embodiment, a transparent covering 140 is provided to enable viewing of the windows 136 and 138 without contamination of the test strips.

As described previously, an air outlet (not shown) is preferably provided on the cap to dissipate any pressure which may build up as the liquid moves along the test strip and deposited in second wick pads 130. Such air outlet may comprise a gap along the perimeter of the covering 140, or one or more holes therein. In one embodiment, the cover 140 is omitted thereby exposing the cover 108 of the cap. In such case, the test strips are exposed to the outside by means of windows 136 and 138 which, therefore, provide the air outlet for the device. In another embodiment, an outlet for the air being displaced during the assay may be achieved by providing one or more holes 154 in the bottom wall 115 of the middle portion 106. Such holes will allow the passage of air while preventing passage of the liquid (due to its surface tension) therethrough. In such arrangement, the holes in the wall 115 will allow the displaced air to enter the well 110 thereby avoiding the necessity for air outlets exposed to the outside. Such holes will therefore result in a sealed container and avoid the possibility of the liquid leaking therefrom.

A valve member, or seal pad 142 is provided between the base 102 and the middle portion 106. The seal pad 142 is positioned within a space 144 bounded by the wall 116 of the base 102 and an opposing bearing surface 146 formed by a plurality of indentations 148 formed in the middle portion 106 of the cap as shown in FIGS. 1 and 13. The space 144 for the seal pad is also bounded by oppositely facing corners 148 on the top surface of the base 102 as shown in FIGS. 7 and 8. Such corners prevent movement of the seal pad 142 by engaging the lower corners thereof. To further immobilize the seal pad, there may be provided further corners etc. The seal pad 142 is placed adjacent the window 114 on wall 116. The seal pad is generally made of a swellable material which absorbs the liquid entering the well 110 and begins swelling. As the seal pad 142 expands, bearing wall 146 forces the pad against the opposite wall 116 and, therefore, against the window 114. It will be appreciated that the wall 116 and, the corners 148 and the upper wall 115 force the seal pad to expand only in the direction of the window 114. Upon expanding a sufficient amount, the seal pad 142 thereby closes the window 114 and prevents further liquid from entering the well 110 and effectively seals the liquid contents of the container from contamination. In the preferred embodiment as shown in FIG. 7, the wall 116 is sloped and the bearing surface 146 is parallel to same. In such arrangement, when the container is in the upright position, the seal pad 142 rests upon the wall 116, and, therefore against the window 114. Similarly, when in the upside down position, the seal pad, when in the non-expanded form, rests against the bearing surface 146. In the preferred embodiment, the wall 116 is angled at 30°.

Figure 14:
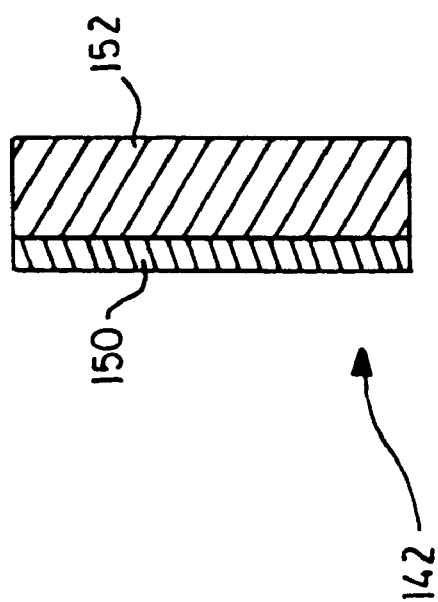
FIG. 14 is a side cross sectional view of the seal pad of FIG. 7.

As shown in FIGS. 7 and 14, the seal pad 142 is laminated and comprises of first and second layers 150 and 152, respectively. First, or sealing layer 150 is preferably a foam material such as cross-linked polyolefin foam. The second, or expanding layer 152 is formed from an absorbent and expanding material. Preferably, the material forming the second layer 152 undergoes an irreversible expansion whereby its expanded form is maintained when the absorbed liquid is evaporated over time. The choice of the material for the second layer 152 will depend upon the nature of the liquid being assayed. In the case of an aqueous liquid, the preferred material for such second layer is balsa wood. It will be appreciated that some materials cannot be used for certain assays as they may bind with the analytes being tested and, therefore, render a false negative result. The material for the first layer 150 is chosen to provide an adequate seal to close the window 114 and, thereby, preventing liquid from entering or leaving the well 110.

It will be appreciated that the thickness of the seal pad depends upon various factors. For example, a pad that is too thick after expansion will seal the window before a sufficient volume of the liquid is collected in the well. Similarly, a pad that is too thin after expansion will not effectively seal the window. Therefore, the thickness of the seal pad is based on the swellability of the pad material and the width of the space 144 in which it is placed. For example, the following table illustrates the swellability of various materials which may be used in forming the seal pad:

| Material | Condition | Swelling |
| --- | --- | --- |
| PEBAX | Natural | 18% |
| PEBAX | Natural | 18% |
| PEBAX | Natural | 17% |
| Balsa wood | Natural | 3% |
| Balsa wood | Hot pressed | 31% |
| Balsa wood | Hot pressed (with foam layer) | 8% |
| Balsa wood | Hot pressed (with foam layer) | 8% |
| Balsa wood | Cold pressed (with foam layer) | 36% |
| Balsa wood | Cold pressed (with foam layer) | 37% |

In a cap for a conventional container, a seal pad, as shown in FIG. 14, is a total of 0.125" in width, and has a sealing layer comprised of cross linked polyolefin of width 0.03" and an expanding layer comprised of balsa wood of width 0.095". Further, in the case of balsa wood being used as the expanding layer, full swelling of the seal pad normally takes approximately 15 minutes.

In a preferred embodiment, the various portions of the cap 100, the base 102, the middle portion 106 and the cover 108, are attached together by conventional means. In such manner, the various non-structural elements, the wick 120, the wick pads 128 and 130, the test strips 124 and the seal pad 142, are maintained in a fixed position.

Figure 16:
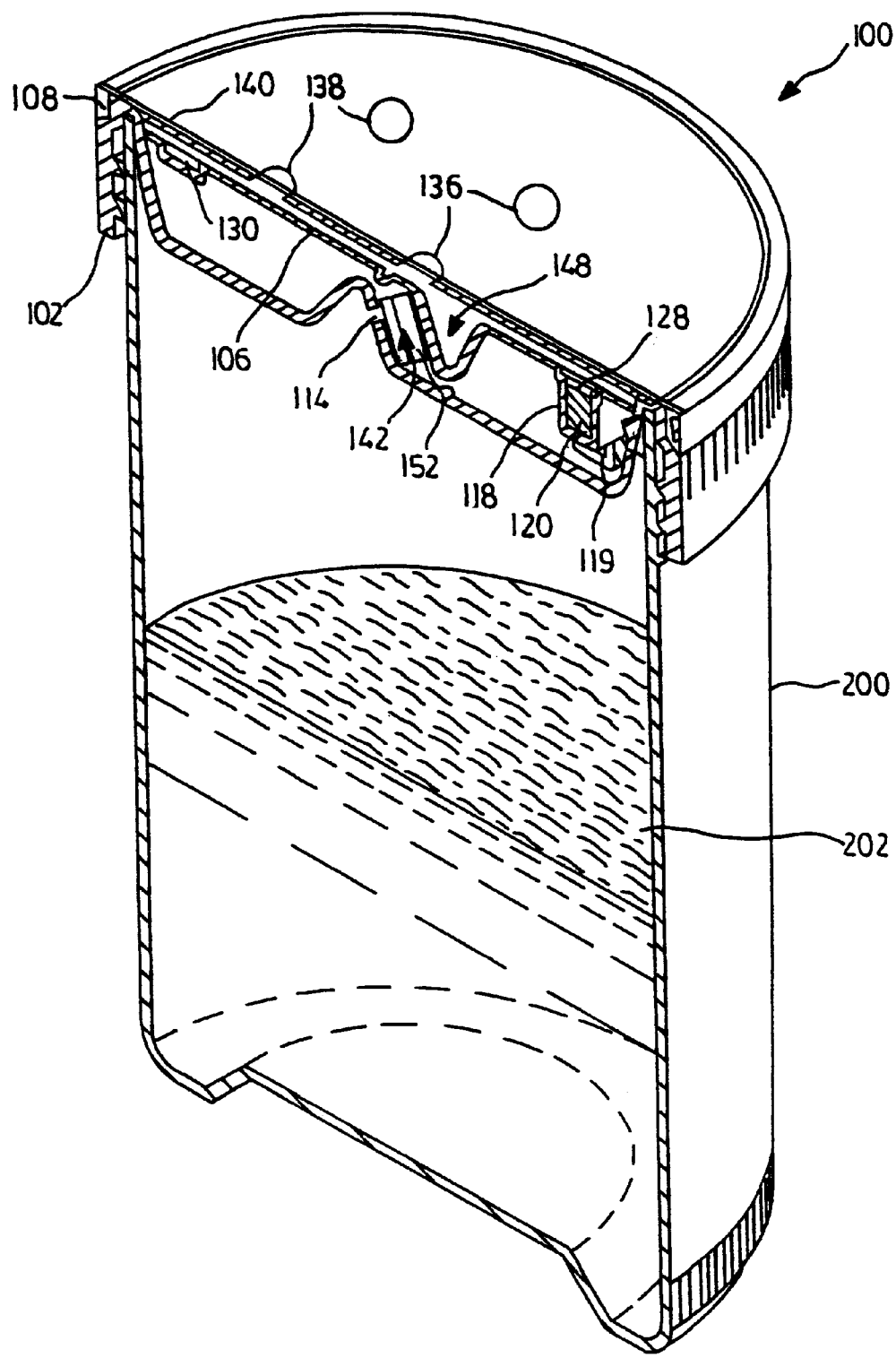
FIG. 16 is a perspective view of the embodiment of FIG. 7.

FIG. 16 illustrates the positioning of the cap 100 on a conventional container 200 for specimens containing liquid 202 to be tested.

In another embodiment, a raised portion 156 is provided on the side wall 116 on the surface facing the seal pad 142. Raised portion 156 serves to prevent the seal pad from floating upwards against window 114 while the well 110 is being filled. Such raised portion is not, however, so large as to prevent closure of the window after expansion of the seal pad. During the swelling of the pad, the flexible nature thereof will surround the raised portion 156.

The use of the assay device of FIG. 7 is similar to that discussed above. Firstly, the cap is removed and a volume of the liquid to be tested in added to the container. The cap 100 is then replaced onto the container. When the assay is required, the container in the closed position is turned upside down thereby causing the liquid to collect on the cap 100 and enter the inlet portion 112 of the base 102. The liquid then passes through the window 114, over the seal pad 142 and onto the top wall 115 of the well 110 where it is collected. It will be appreciated that the top wall 115 prevents the liquid sample from contacting the test strips 124. While the top portion of the well 110 is filling, the seal pad gradually expands and, as discussed above, eventually seals window 114 thereby preventing further liquid from entering the well 110. Also as mentioned above, the window 114 is positioned a sufficient distance from the bottom surface 115 of the middle portion 106 so that a sufficient volume of liquid can be collected within the well.

After the window is sealed, the container is turned right side up and the collected liquid 111 is maintained within the well 110. As will be appreciated, a smaller volume of liquid will be collected within the well if the window 114 is close to the bottom wall 115, that is, the upper surface of the well, than if the window is closer to the bottom wall 113 of the well.

The wick 120 is then allowed to absorb the liquid and, by capillary action, transfer such liquid to the first wick pad 128. The liquid is then transferred, again by capillary action, across the test strip 124 and is collected at the second wick pad 130. As mentioned above, the test strip is treated with various reagents depending upon the assay being conducted. Further, in the preferred embodiment, a plurality of different test strips can be provided on the cap 100 thereby permitting various assays to be simultaneously conducted on a given sample.

In a preferred embodiment, the position of the window along the wall 116 can be determined based on the volume of liquid to be collected. As mentioned above, if the window is positioned close to wall 115, a lesser volume will be collected than if the window is positioned close to the bottom wall 113 of the well. Therefore, it is possible to pre-determine the volume of the sample collected by the appropriate positioning of the window. Further, in the preferred embodiment, the window is positioned above the bottom of the chamber 118 when in the upright position. In such arrangement, when the reservoir is being filled, the liquid sample level will be maintained below the opening of the wick chamber 118 thereby preventing the liquid from contacting the wick. Therefore, with this type of arrangement the wick is wetted, and the assay begun, only after the device is turned upright.

As discussed previously, the embodiment described above can be used in various applications where testing of a liquid is required. For example, the device can be used for analyzing body fluids such as urine for the presence of various substances. Similarly, the device can be used for testing of water samples for pollutants, toxins and other such substances.

It will be appreciated that the volume of liquid collected within the reservoir will be dependent upon the number of test strips contained within the assay device since each strip absorbs a volume of the liquid. Therefore, a device having one strip will require less of a liquid sample than a device having five strips as shown in the drawings of the preferred embodiments. The volume of the sample collected in the reservoir is based on various criteria. For example, as mentioned above, the positioning of the window 114 along the wall 116 is one such factor. In addition, the depth of the reservoir would also affect the quantity of the liquid available for the assay procedure.

In a further embodiment of the invention, the container is sealed thereby preventing leakage of the liquid contents and is provided with holes in the middle portion 106 as described above. In this embodiment, the seal pad 142 is omitted. Such a version of the invention can be utilized where a segregation of the liquid in the container and that being assayed is not required. An example of such use is in the testing of samples from bodies of water.

As will be apparent to those skilled in the art in the light of the foregoing disclosure, many alterations and modifications are possible in the practice of this invention without departing from the spirit or scope thereof. Accordingly, the scope of the invention is to be construed in accordance with the substance defined by the following claims.

The embodiments of the invention in which an exclusive property or privilege is claimed are defined as follows:

1. An apparatus for conducting an assay on a liquid located in a container, the apparatus comprising:
    a removable cap for closing the container;
    at least one assaying device located on the cap for visual observation thereof, the assaying device having means for analyzing said liquid and visually displaying the presence of specific analytes in the sample liquid;

a reservoir attached to the cap, the reservoir defining a chamber communicating with the assaying device, the reservoir having a wall defining at least one opening for collecting a predetermined volume of sample liquid inside the chamber upon submerging the reservoir in the sample liquid;

a means for supplying said liquid collected in said sub-chamber to said assaying device;

a valve member located between the reservoir chamber and the assaying device, the valve member being formed of material that absorbs the liquid and swells thereby sealing the assaying device from the chamber after a predetermined amount of sample liquid supplied to the assaying device.

2. An apparatus according to claim 1 wherein the cap has a top surface and a bottom surface, the reservoir being connected to the bottom surface of the clip, the assaying device being supported on the top surface of the cap.

3. A method of conducting an assay on a liquid comprising the steps of:
a) collecting a sample of the liquid to be assayed in a container having a removable cap wherein said cap includes a sub-chamber and an assaying device having a means for chemically analyzing a liquid for a specific analyte, and wherein said cap includes a passage for connecting the sub-chamber with said container, said passage including a barrier capable of being expanded upon contact with said liquid;
b) segregating a portion of said liquid into said sub-chamber;
c) contacting said barrier with said portion of the liquid for expanding said barrier to hermetically seal said passage; and
d) contacting said portion of the liquid with said assaying device whereby said sample is assayed for said analyte.

4. An assay device for a liquid contained within a container, said device comprising a removable cap for said container, said cap having:
a reservoir to receive a sample of said liquid from the container;
a passage for transferring said sample of liquid from said container to said reservoir;
a means for closing said passage to separate said sample from the remainder of the liquid;
a means for assaying said liquid sample;
a means for transferring said liquid sample from said reservoir to said means for assaying.

5. An assay device as claimed in claim 4 wherein said means for closing comprises a swellable material which swells upon absorbing said liquid and bears against said passage.

6. An assay device as claimed in claim 4 wherein said means for transferring said liquid comprises a wick which is contacted with said liquid sample in said reservoir.

7. An assay device as claimed in claim 4 wherein said means for closing comprises a laminated slab having at least one swellable layer which swells upon absorbing said liquid.

8. An assay device as claimed in claim 7 wherein said slab includes at least one sealing layer which seals said passage.

9. An assay device as claimed in claim 8 wherein said cap further includes a bearing surface opposite said opening and wherein said closing means is located between said passage and said bearing surface.

10. An assay device as claimed in claim 9 wherein said swellable layer comprises balsa wood.

11. An assay device as claimed in claim 10 wherein said sealing layer comprises cross-linked polyolefin foam.

12. An assay device as claimed in claim 4 wherein said means for assaying said liquid sample comprises a plurality of test strips.

13. An assay device as claimed in claim 12 wherein said test strips include a first wick pad, an elongate assay surface and a second wick pad and wherein said first and second wick pads are located at opposite ends of said assay surface.

14. An assay device as claimed in claim 13 wherein said strips extend substantially along the diameter of said cap.

15. An assay device as claimed in claim 14 wherein said means for transferring said liquid comprises a wick which is contacted with said liquid sample in said reservoir.

16. An assay device as claimed in claim 15 wherein said wick transfers said liquid sample to said first wick pad.

17. An assay device as claimed in claim 16 wherein said means for closing comprises a swellable material which swells upon absorbing said liquid and bears against said passage.

18. An assay device as claimed in claim 16 wherein said means for closing comprises a laminated slab having at least one swellable layer which swells upon absorbing said liquid.

19. An assay device as claimed in claim 18 wherein said slab includes at least one sealing layer which seals said passage.

20. An assay device as claimed in claim 19 wherein said cap further includes a bearing surface opposite said opening and wherein said closing means is located between said passage and said bearing surface.

21. An assay device as claimed in claim 20 wherein said swellable layer comprises balsa wood.

22. An assay device as claimed in claim 21 wherein said sealing layer comprises cross-linked polyolefin foam.

23. An assay device as claimed in claim 22 further including a cover for covering said test strips and through which said strips are observed.

24. An assay device for a liquid contained within a container, said device comprising a removable cap for said container, said cap having:
a reservoir to receive a sample of said liquid from the container;
a passage for transferring said sample of liquid from said container to said reservoir;
a valve for closing said passage to separate said sample from the remainder of the liquid;
one or more test strips for assaying said liquid sample;
a wick for transferring said liquid sample from said reservoir to said test strips.

25. A method of assaying a liquid using a device as claimed in claim 24, the method comprising:
a) collecting said liquid in said container;
b) inverting said container to allow said liquid sample to enter said reservoir through said passage;
c) returning said container to an upright position thereby allowing said wick to contact said liquid sample;
d) monitoring said test strips for the assay.

26. An assay device as claimed in claim 24 wherein said test strips comprise chromatographic or chemi-luminescent test strips.

27. An apparatus as claimed in claim 24 wherein said valve comprises a laminate, at least one layer of which is swellable upon absorbing said liquid.

28. An apparatus as claimed in claim 27 wherein said at least one layer is balsa wood.

* * * * *